(12) United States Patent
Draenert

(10) Patent No.: US 11,589,962 B2
(45) Date of Patent: Feb. 28, 2023

(54) METHOD FOR THE NON-INVASIVE FRAGMENTATION OF RESIDUAL BIOMATERIAL AFTER BONE AUGMENTATION

(71) Applicant: Florian Draenert, Munich (DE)

(72) Inventor: Florian Draenert, Munich (DE)

(*) Notice: Subject to any disclaimer, the term of this patent is extended or adjusted under 35 U.S.C. 154(b) by 693 days.

(21) Appl. No.: 16/612,041

(22) PCT Filed: May 9, 2018

(86) PCT No.: PCT/EP2018/062085
§ 371 (c)(1),
(2) Date: Nov. 8, 2019

(87) PCT Pub. No.: WO2018/206686
PCT Pub. Date: Nov. 15, 2018

(65) Prior Publication Data
US 2020/0163744 A1    May 28, 2020

(30) Foreign Application Priority Data

May 10, 2017  (EP) .................................... 17170502
Nov. 17, 2017  (EP) .................................... 17202460

(51) Int. Cl.
*A61C 8/00* (2006.01)
*A61N 7/00* (2006.01)
*A61B 17/22* (2006.01)
*A61C 8/02* (2006.01)

(52) U.S. Cl.
CPC ...... *A61C 8/0089* (2013.01); *A61B 17/22004* (2013.01); *A61C 8/0086* (2013.01); *A61N 7/00* (2013.01); *A61C 8/0006* (2013.01); *A61N 2007/006* (2013.01); *A61N 2007/0013* (2013.01)

(58) Field of Classification Search
CPC ... A61C 8/0089; A61C 8/0086; A61C 8/0006; A61B 17/22004; A61B 2017/22005; A61N 7/00; A61N 2007/0013; A61N 2007/006
See application file for complete search history.

(56) References Cited

U.S. PATENT DOCUMENTS

| | | | |
|---|---|---|---|
| 4,655,220 | A | 4/1987 | Hahn et al. |
| 5,224,468 | A | 7/1993 | Grünewald et al. |
| 5,316,000 | A | 5/1994 | Chapelon et al. |
| 7,497,835 | B2 | 3/2009 | Schultheiss et al. |
| 2003/0093013 | A1 | 5/2003 | Zhong et al. |

(Continued)

FOREIGN PATENT DOCUMENTS

| DE | 10 2011 011124 B3 | 7/2012 |
|---|---|---|
| JP | 01 91843 A | 4/1989 |

OTHER PUBLICATIONS

Invitation to Pay Additional Fees, and Where Applicable, Protest Fee received from related International Application No. PCT/EP2018/062085 dated Jul. 13, 2018.

(Continued)

*Primary Examiner* — Hien N Nguyen
(74) *Attorney, Agent, or Firm* — The Marbury Law Group, PLLC

(57) ABSTRACT

The invention relates to a method for the non-invasive fragmentation of residual biomaterial after bone augmentation, and to a device specifically adapted for said method.

19 Claims, 3 Drawing Sheets

(56) References Cited

U.S. PATENT DOCUMENTS

| | | | |
|---|---|---|---|
| 2004/0030326 A1* | 2/2004 | Altshuler | A61C 1/0046 606/13 |
| 2006/0036194 A1* | 2/2006 | Schultheiss | A61H 23/008 601/2 |
| 2008/0003536 A1* | 1/2008 | Altshuler | A61C 1/0046 433/29 |
| 2008/0228112 A1* | 9/2008 | Voss | A61H 1/008 601/4 |
| 2010/0160838 A1* | 6/2010 | Krespi | A61B 18/26 604/20 |
| 2010/0160903 A1* | 6/2010 | Krespi | A61B 18/26 606/7 |
| 2011/0207075 A1* | 8/2011 | Altshuler | A61L 27/46 433/29 |
| 2012/0215138 A1 | 8/2012 | Zhong et al. | |
| 2012/0308956 A1* | 12/2012 | DeVengencie | A61C 17/20 433/119 |
| 2013/0137059 A1 | 5/2013 | Jo | |
| 2015/0044628 A1* | 2/2015 | Flyash | A61C 17/16 433/32 |
| 2015/0238755 A1* | 8/2015 | Fregoso | A61N 1/0448 433/32 |
| 2017/0112524 A1 | 4/2017 | Smith et al. | |

OTHER PUBLICATIONS

International Search Report and the Written Opinion of the International Searching Authority received in related Application No. PCT/EP2018/062085 dated Sep. 17, 2018.

Written Opinion of the International Searching Authority received in related International Application No. PCT/EP2018/062085 received from the European Patent Office dated Jan. 2015.

Sanz M, Vignoletti F. "Key aspects on the use of bone substitutes for bone regeneration of edentulous ridges." Dent Mater. 2015;31:640-647.

Esposito M, Grusovin MG, Kwan S, Worthington HV, Coulthard P. "Interventions for replacing missing teeth: bone augmentation techniques for dental implant treatment." Cochrane database of systematic reviews. 2008: CD003607.

Draenert FG, Huetzen D, Neff A, Mueller WE. "Vertical bone augmentation procedures: basics and techniques in dental implantology." Journal of biomedical materials research. Part A. 2014;102:1605-1613.

Fretwurst T, Spanou A, Nelson K, Wein M, Steinberg T, Stricker A. "Comparison of four different allogeneic bone grafts for alveolar ridge reconstruction: a preliminary histologic and biochemical analysis." Oral Surg Oral Med Oral Pathol Oral Radiol. 2014;118:424-431.

Zimmermann G, Moghaddam A. "Allograft bone matrix versus synthetic bone graft substitutes." Injury. 2011;42 Suppl 2:S16-21.

Draenert GF, Delius M. "The mechanically stable steam sterilization of bone grafts." Biomaterials. 2007;28:1531-1538.

Finkemeier CG. "Bone-grafting and bone-graft substitutes." Journal of Bone & Joint Surgery America. 2002;84-A:454-464.

Simion M, Nevins M, Rocchietta I, et al. "Vertical ridge augmentation using an equine block infused with recombinant human platelet-derived growth factor-BB: a histologic study in a canine model." Int J Periodontics Restorative Dent. 2009;29:245-255.

Muller WE, Wang X, Diehl-Seifert B, et al. "Inorganic polymeric phosphate/polyphosphate as an inducer of alkaline phosphatase and a modulator of intracellular Ca2+ level in osteoblasts (SaOS-2 cells) in vitro." Acta Biomaterialia. 2011;7:2661-2671.

Williams D. "The continuing evolution of biomaterials." Biomaterials. 2011;32:1-2.

Costello BJ, Shah G, Kumta P, Sfeir CS. "Regenerative medicine for craniomaxillofacial surgery." Oral Maxillofac Surg Clin North Am. 2010;22:33-42.

Huebsch N, Mooney DJ. "Inspiration and application in the evolution of biomaterials." Nature. 2009;462:426-432.

Luong-Van E, Grondahl L, Chua KN, Leong KW, Nurcombe V, Cool SM. "Controlled release of heparin from poly(epsilon-caprolactone) electrospun fibers." Biomaterials. 2006;27:2042-2050.

Delloye C, Cornu O, Druez V, Barbier O. "Bone allografts: What they can offer and what they cannot." J Bone Joint Surg Br. 2007;89:574-579.

Nissan J, Marilena V, Gross O, Mardinger O, Chaushu G. "Histomorphometric analysis following augmentation of the posterior mandible using cancellous bone-block allograft." J Biomed Mat Res A. 2011e;97A:509-513.

Spin-Neto R, Landazuri Del Barrio RA, Pereira LA, Marcantonio RA, Marcantonio E, Marcantonio E, Jr. "Clinical similarities and histological diversity comparing fresh frozen onlay bone blocks allografts and autografts in human maxillary reconstruction." Clin Implant Dent Relat Res. 2013;15:490-497.

Khoury F, Hanser T. Mandibular bone block harvesting from the retromolar region: a 10-year prospective clinical study. The International journal of oral & maxillofacial implants. 2015;30:688-397.

Gellrich NC, Held U, Schoen R, Pailing T, Schramm A, Bormann KH. "Alveolar zygomatic buttress: A new donor site for limited preimplant augmentation procedures." Journal of Oral & Maxillofacial Surgery. 2007;65:275-280.

Nissan J, Ghelfan O, Mardinger O, Calderon S, Chaushu G. "Efficacy of cancellous block allograft augmentation prior to implant placement in the posterior atrophic mandible." Clin Implant Dent Relat Res. 2011a;13:279-285.

Simion M, Jovanovic SA, Tinti C, Benfenati SP. "Long-term evaluation of osseointegrated implants inserted at the time or after vertical ridge augmentation. A retrospective study on 123 implants with 1-5 year follow-up." Clin Oral Implants Res. 2001;12:35-45.

Iglhaut G, Schwarz F, Grundel M, Mihatovic I, Becker J, Schliephake H. "Shell technique using a rigid resorbable barrier system for localized alveolar ridge augmentation." Clin Oral Implants Res. 2014;25:e149-154.

Schliephake H, Drewes M, Mihatovic I, Schwarz F, Becker J, Iglhaut G. "Use of a self-curing resorbable polymer in vertical ridge augmentations—a pilot study in dogs." Clin Oral Implants Res. 2014;25:435-440.

Urban IA, Jovanovic SA, Lozada JL. "Vertical ridge augmentation using guided bone regeneration (GBR) in three clinical scenarios prior to implant placement: a retrospective study of 35 patients 12 to 72 months after loading." Int J Oral Maxillofac Implants. 2009;24:502-510.

Delius M, Draenert K, Al Diek Y, Draenert Y. "Biological effects of shock waves: in vivo effect of high energy pulses on rabbit bone." Ultrasound Med Biol. 1995;21:1219-1225.

Haupt G., Habilitation Thesis 1997—English language analog and concise summary provided by Haupt G. "Use of Extracorporeal Shock Waves in the Treatment of Pseudarthrosis, Tendinopathy and Other Orthopedic Diseases." The Journal of urology, vol. 158, 1997, submitted herewith as item No. 29.

Haupt G. "Use of Extracorporeal Shock Waves in the Treatment of Pseudarthrosis, Tendinopathy and Other Orthopedic Diseases." The Journal of urology, vol. 158, 1997, DO—10.1097/00005392-199707000-00003—english language analog and concise summary of thesis submitted herewith as item No. 28.

* cited by examiner

METHOD FOR THE NON-INVASIVE FRAGMENTATION OF RESIDUAL BIOMATERIAL AFTER BONE AUGMENTATION

CROSS-REFERENCE TO RELATED APPLICATIONS

This application claims priority to, and is the 35 U.S.C. § 371 U.S. National Phase of, Patent Cooperation Treaty application no. PCT/EP2018/062085 filed on May 9, 2018 which claims the benefit from the priorities of European patent applications EP 17170502.3 of May 10, 2017 and EP 17202460.6 of Nov. 17, 2017; the entire contents of all three of these applications are hereby incorporated by reference.

BACKGROUND OF THE INVENTION

1. Technical Field

The invention relates to a method for the non-invasive fragmentation of residual biomaterial after bone augmentation and to a device, which is specifically adapted to said method.

2. Background Information

Alveolar ridge reconstructions including vertical augmentations are challenging procedures in dental implantology and can be summarized as complex bone augmentations [1]. These techniques require a mechanical stabilization of the augmented area due to the lack of natural support by the bony wall of the alveolar ridge.

The material concept is a far more difficult area with various opinions and colliding points of view amongst specialists due to a controversial scientific data situation [2]. Current techniques vary amongst different clinics mostly depending on the surgical skills and the level of understanding for the biology of bone on the side of the treating surgeon. Gold standard is the autologous bone block [3]. While cancellous bone in sufficient volumes can only be obtained from distant donor regions, it is possible to harvest cortical bone blocks locally. Cortical bone cannot remain as living tissue transplant containing vital cells without blood supply. Massive cortical blocks are therefore subject to complete resorption and remodeling with an associated long time course of complete healing and risk of complications over several years. This results in high fracture risk of the blocks and hardly predictable resorption.

Biomaterial blocks with interconnecting porous system, analogous to natural cancellous bone are an approach to address this issue. Mechanical stability and elasticity properties of appropriate materials must allow drilling and screwing for fixation at the site of augmentation. One group of the two material types in this category are natural, non-deproteinized, mineralized bone matrices of xenogenic or allogeneic origin (MBM) [2, 4-8]. The other group consists of artificial blocks with interconnecting porous system made from various appropriate materials like chitosan, polycaprolactone, polyphosphates, and others, that are often tested in the field of in vitro tissue engineering in combination with cells and not a clinical standard today [9-13]. Resorption is incomplete in these matrices, contrary to autologous cancellous bone. New bone is formed in a shell like way along the existing trabeculae that become resorbed during this process until the new bone layer is stable and functional. This results in residual material underneath the newly formed bone. Well-documented human histologies showed this effect in allogeneic bone blocks [14-16]. Nissan at al. proved a percentage of 29% non-resorbed allogeneic matrix residues under the newly formed bony ingrowth after 6 months [15]. This result is different from autologous bone grafts that are in fact also non-vital but become remodeled fast. Spin-Neto et al. observed an advanced stage of remodeling and less or no residual graft material in autologous bone and a high rate of residual material with less advanced healing and multiple sites of necrotic bone in allogeneic grafts after 7 months (n=17 allogeneic and n=12 autologous) [16]. It must be presumed that the problem of residual biomaterial is true for other osteoconductive materials as well.

Shell techniques use only a thin shell of stiff material to stabilize a particulate graft that can consist of 100% autologous bone chips or a mesh graft containing particulate, resorbable biomaterial additionally to fill large volumes. This approach reduces the critical material issue to a thin shell that can be completely circumvented or removed crestally at the time of implantation [1, 17-23]. Shell techniques are surgically more difficult and therefore biomaterial blocks with interconnecting porous systems either of natural or artificial origin are more favorable if the problem of residual material could be solved. A solution for this problem could also become applicable to monophasic ceramics, polymers and other bone matrices with interconnecting porous system all bearing the same problem of residual material and the associated risk of early severe periimplantitis after prosthetic loading.

Said biomaterial blocks with interconnecting porous systems can include mentioned appropriate biomaterials and will be abbreviated BIPS (biomaterial blocks with interconnecting porous system).

Therefore, the problem underlying the present invention was to provide a non-invasive method to reduce or remove residual biomaterial after bone augmentation.

It is known from orthopedics that shock waves can be applied in various chronic bone and joint problems as a non-invasive physical therapy. Further experimental work shows an effect in bone that is the basis of the inventory idea of the presented method and device. Shock waves have been shown to result in micro-fractures in the cancellous bone trabeculae when applied there [24]. In this animal experiment 1500 shock wave pulses at 27.5 kV with a capacitance of 80 nF were applied at 1 Hz. Micro-fractures in the bone were shown in this study.

It is deduced from this observation that micro-fractures also occur within a biomaterial block with interconnecting porous system and that this aseptic micro-injury leads to a new healing process in the biomaterial area that results in a more complete resorption of residual biomaterial.

This problem has been solved according to this invention by fragmentation of the biomaterial after bone augmentation with the aid of shock waves.

BRIEF SUMMARY OF THE INVENTION

Therefore, the invention relates to a method for the non-invasive fragmentation of residual biomaterial after bone augmentation which comprises generating shock waves; applying said shock waves transdermal or intraorally; and
targeting said shock waves toward said residual biomaterial.

Furthermore, the invention relates to a shock wave generator specifically adapted to said method.

DETAILED DESCRIPTION OF THE INVENTION

Figure 1:
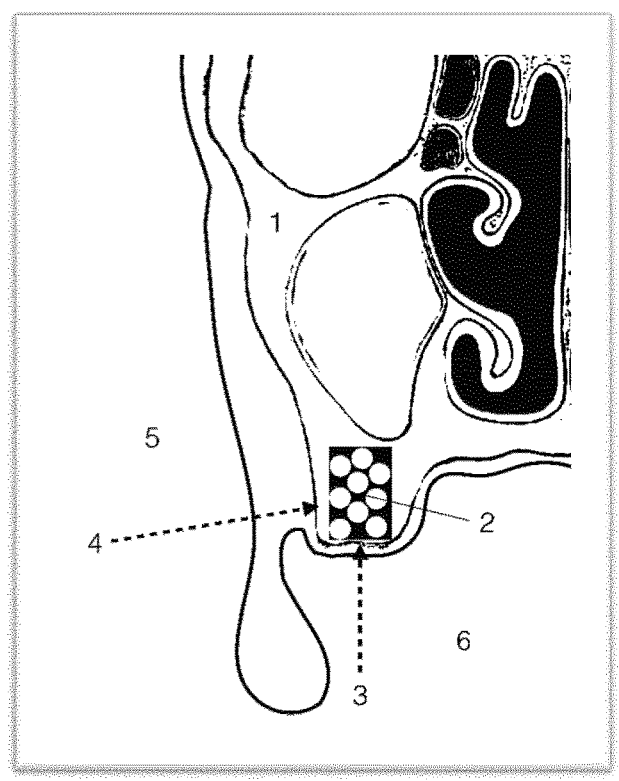
FIG. 1 shows a coronal cut transection of the skull with the maxillary bone and a biomaterial block osseointegrated in the alveolar bone.

The bone augmentation relates to those applied biomaterial blocks with interconnecting porous system as described above (BIPS).

The related biomaterial blocks are osteoconductive and thus support the bony ingrowth of newly formed bone into the matrix.

The related biomaterial blocks (BIPS) are preferably mineralized bone matrices (MBM), including allogeneic or xenogeneic ones, artificial biomaterial with interconnecting porous system or said biomaterial blocks containing collagen or other proteins or other resorbable biomaterials, including ceramics like tricalcium phosphate and silicates, biopolymers selected from the group consisting of polycaprolactone, polylactides and polysilicates, or chitosan or sugar-polymers.

The related biomaterial blocks alternatively may be non-resorbable BIPSs, including ceramics like hydroxylapatite or xenogenic ceramics or non-resorbable material types of the above mentioned.

The related biomaterial blocks alternatively may be other biomaterials with osteoconductive properties.

The described shock wave application relates to the application of this technology in urology known as Extracorporeal Shock Wave Lithotripsy (ESWL). Shock waves in ESWL have typically a broad frequency spectrum between 20 kHz and some MHz. Most energy is between 100 kHz and 1 MHz with a peak at 300 kHz. Shock waves are typically applied in pulsed dosing to allow a calculated energy application with less heat generation, e.g. US patent application US 2012/0215138 A1 and US patents cited therein. The strong application of a short shock wave leads to mechanical disruption of stiff structures as urea stones and to cavitation effect associated with it. This leads to pressures between 30 and 150 MPa for 0.5-3 microseconds, after a rise time of around 10 ns and a following decompression with a negative pressure peak of approximately −30 MPa over 2-20 microseconds. Pulse energies are in a range of 10 to 100 mJ and energy densities are between about 0.2 and 2.0 mJ/mm$^2$ whereby energy density is defined as the amount of acoustical energy transmitted through an area of 1 mm$^2$ per pulse.

Said pulses of shockwaves are applied in fast repetition (short pulse shockwave).

Further embodiments of the present invention are the following methods, wherein:

(A) said method is applied in dental implantology or orthopedic surgery after bone augmentation with biomaterials.

(B) said method is applied in orthopedic surgery after bone augmentation with biomaterials in the spin or the tibia head or after hip revision arthroplasty.

(C) said shock waves are applied in the form of pulsed shock waves.

(D) said shock waves are focused toward said residual biomaterial.

(E) said shock waves are applied with the aid of an appropriately angulated device to target the desired area of the alveolar crest intraorally, in particular wherein the angle between the head of the shock wave generator and the handle ranges between 25 and 90 degree.

(F) the residual biomaterial is osteoconductive with an interconnecting porous system and/or resorbable.

All shock wave devices hitherto known are not suitable for intraoral fragmentation of residual biomaterial after bone augmentation in dental implantology, since non-angulated, linear devices cannot be applied easily intraorally.

Accordingly, the invention also relates to an adapted shock wave generator, which focuses the shock wave on the residual biomaterial after bone augmentation in dental implantology with an angulated applicator appropriate for intraoral application.

The focus can be adjusted within the applicator technically by modifying the acoustic lens, or by using a fixed focus and optionally expandable spacer device that is attached to the applicator tip in order adjust it to the calculated distance to the tissue surface and a calculated focus depth thereby.

Preferably the system according to the invention consists of a base station and an applicator hand piece.

The described treatment, of disrupting biomaterial implants to achieve better resorption, can be applied in orthopedic surgery in an analogous ways with the existing medical devices as described above. The main indications in orthopedic surgery incudes: tibia head fractures, fraktures of the vertebral body in spine surgery and osteoplasty of the femur in hip revision arthropasty and other arthroplasty.

Example 1

A Botiss bonebuilder allogeneic spongiosa block is selected respecting the blood group and possible other types to reduce the risk of host versus graft reactions. The block is implanted in a defect area in the jaws to achieve an appropriate bony bed for dental implants. The block is fixed with osteosynthesis screws or other appropriate fixation devices. It is even possible to use the dental implant itself as described as Giesenhagen ring technique.

After an appropriate bony healing period of 3 to 6 months, the following treatment is applied before implantation and prosthetic loading by opening the restoration to the oral cavity via the marginal sulcus.

Implantation is left out in this treatment path, if the implantation was already done simultaneously with the bone block implantation.

Figure 5:
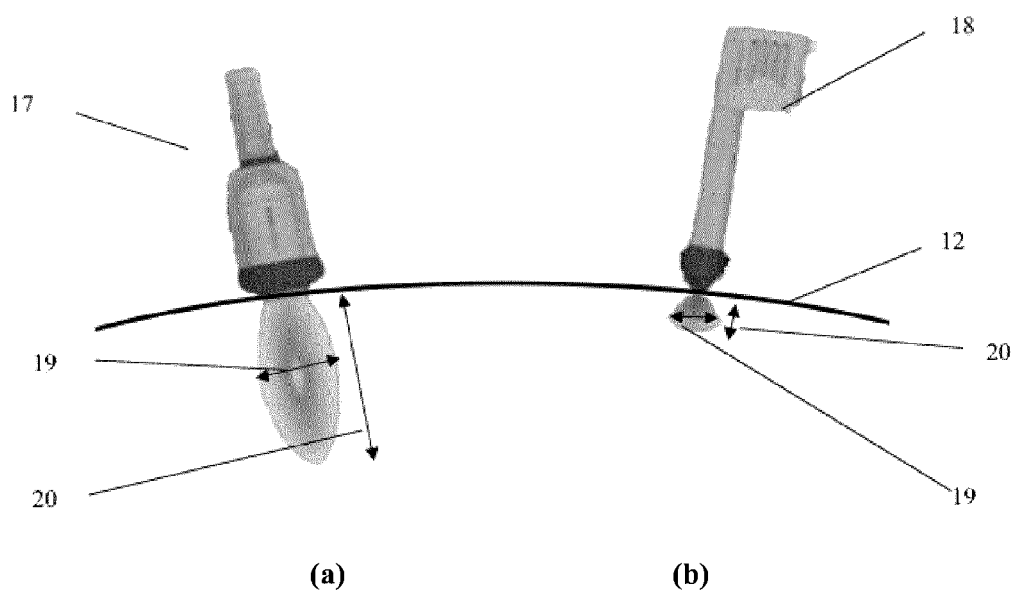
FIG. 5 shows a focused and a radial applicator hand piece with respect and the resulting shock wave width and depth.

A Storz MP200 ESWL base station with 21 Hz and 5.0 bar pressure is applied using a Storz Falcon applicator hand piece. The Falcon hand piece is a radial applicator "pump gun" leading to a less focused but also less deep penetration of the shock waves with the advantage of a wide radial effect area (cp. FIG. 5 (a)). The transmission tip is placed extra-orally on the skin and pressed firmly onto the cheek of the buccal region for the waves to reach the target area in the upper jaw or pressed firmly onto the cheek in the mandibular region for the waves to reach the mandibular alveolar crest and the desired region there. The same can be applied in the front teeth region through the lips.

Example 2

As in Example 1, but wherein the hand piece is replaced by a focused hand piece like the Storz Sepia hand piece "Sniper gun" (cp. FIG. 5 (b)). This allows more focused shock waves achieving a better depth by reducing/narrowing the effect area.

Example 3

As in Examples 1 or 2, wherein the base station is replaced by the Storz Duolith ST.

Example 4

A big mobile urological ESWL unit like the Storz Modulith SLK or a stationary unit like the Storz Modulith SLX-F2 can also be applied in a similar manner by adjusting the patient accordingly to allow the applicator to reach the desired target region in the jaws.

It may be necessary to apply appropriate analgesia including a possible intubation narcosis.

Example 5

As in any of the Examples 1 to 4, but wherein the hand piece is applied at the tibia or the hip area or the spine and targeted to the region with biomaterial osteoplasty.

Figure 2:
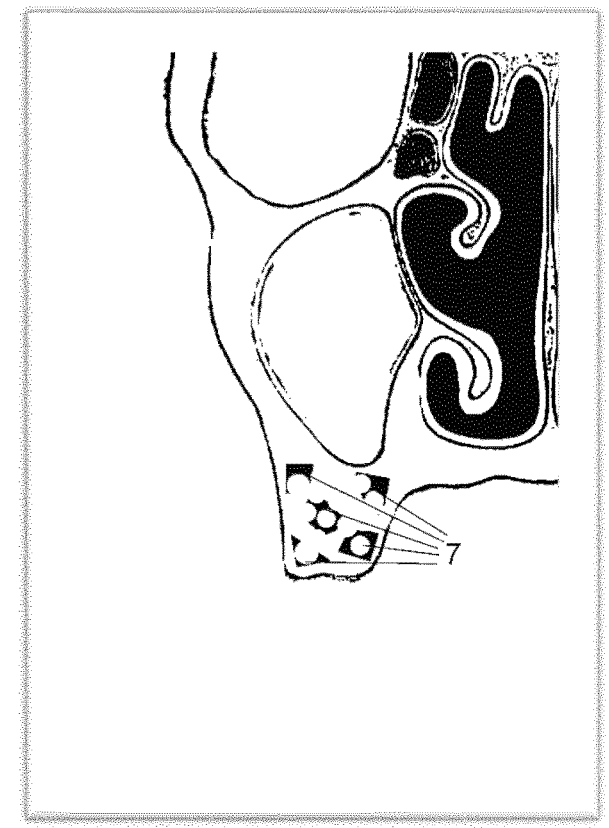
FIG. 2 shows a disrupted biomaterial block pieces that will be partly or totally resorbed during the bone healing process.
Figure 3:
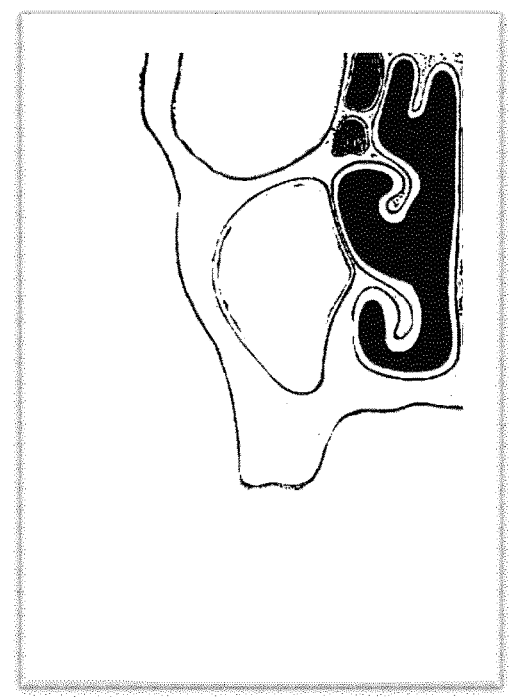
FIG. 3 shows an optimized result with no residual biomaterial left.

The results of the treatments of examples 1 to 4 are shown in the FIGS. 1 to 3.

FIG. 1 shows a coronal cut transection of the skull with the maxillary bone (1) and a biomaterial block (2) osseointegrated in the alveolar bone. Shock waves can be applied transgingival (3) or transdermal (4) through the related spaces, from facial exterior site (5) or from the oral cavity (6).

FIG. 2 shows the disrupted biomaterial block pieces (7) that will be partly or totally resorbed during the bone healing process.

FIG. 3 shows the optimized result with no residual biomaterial left.

Figure 4:
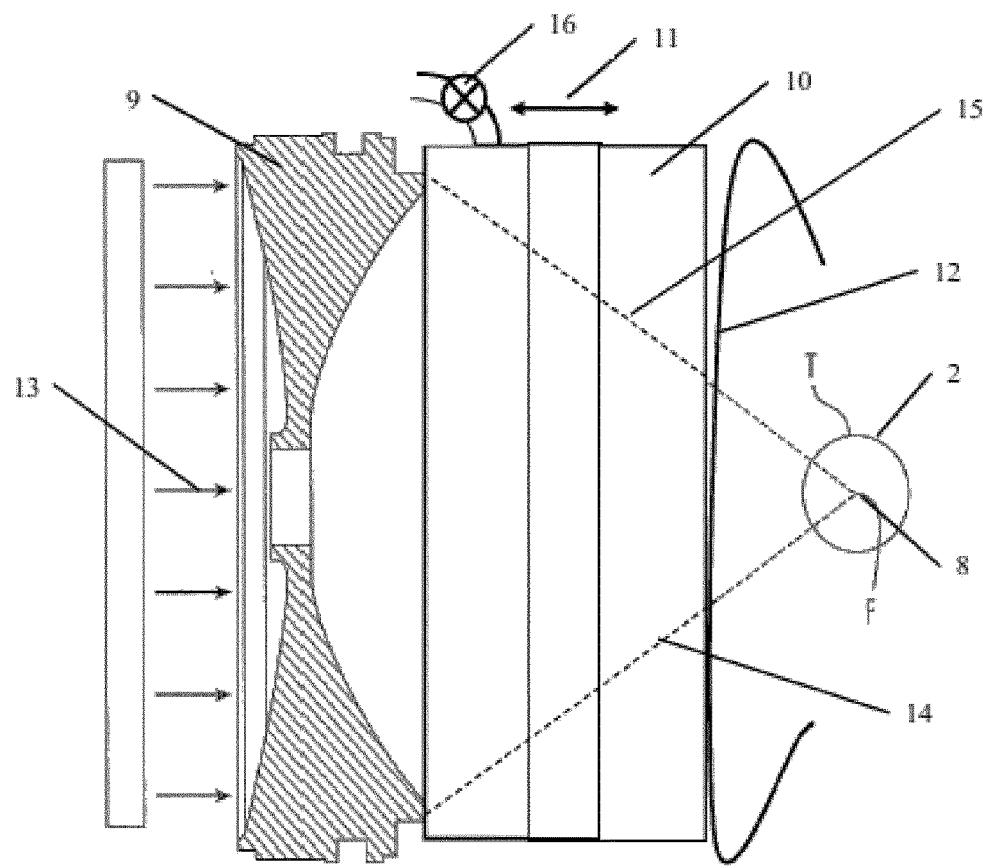
FIG. 4 shows an acoustic lens of a shock wave generator with an adaptor which allows to adjust the focal point/target area of the lens to the position of the target at the implantation site of the biomaterial.

FIG. 4 shows an acoustic lens (9) of a shock wave generator with an expandable distance holder (10), which allows the adjustment of the focal point (8) of the lens with the position of the target at the implantation site of the biomaterial (2). The shock waves (13) are focused (14, 15) by the lens (9). The expansion (11) may be effected by pressurizing the fluid within the distance holder (10) via the inlet valve (16). Therefore, the distance between the lens (9) and the tissue (12) can be adjusted, so that the focal point (8) of the shock wave coincidence with the location of the biomaterial (2).

FIG. 5 shows a focused (17) and a radial applicator (18) hand piece with respect and the resulting shock wave width (19) and depth (20).

Figure 6:
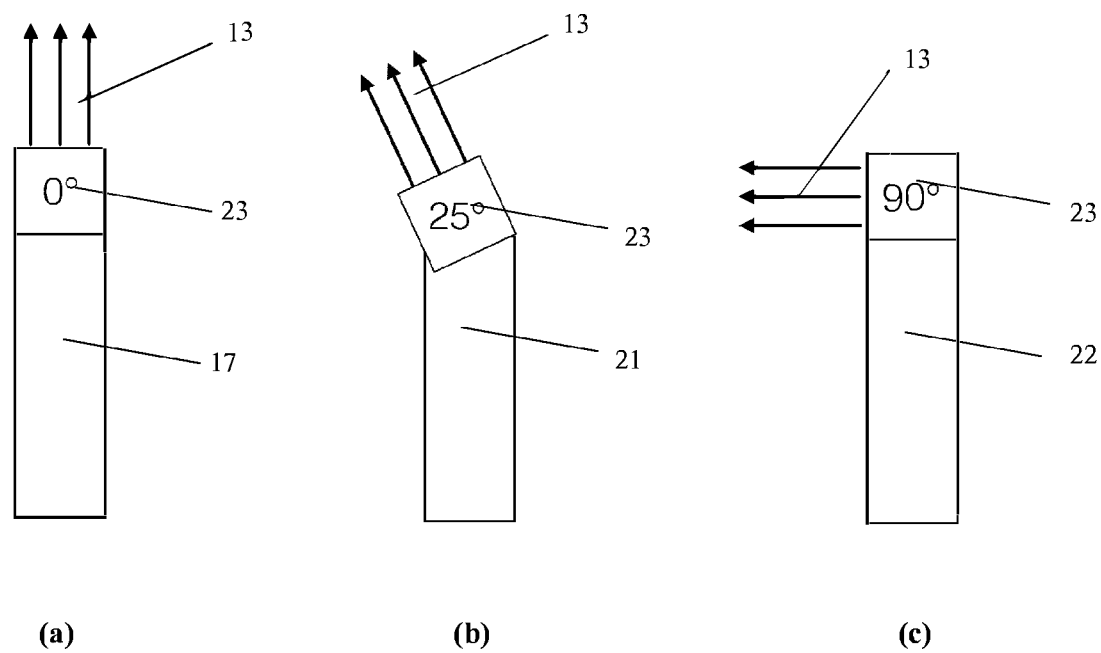
FIG. 6 shows schematic representations of three different hand-held shock wave applicators
(a) represents a hand-held shock wave applicator according to the state of the art
(b) represents a hand-held shock wave applicator according to the invention, wherein the shock wave emitting part of said device forms an angle of 25 degree with the rest of the device;
(c) represents a hand-held shock wave applicator according to the invention, wherein the shock wave emitting part of said device forms an angle of 90 degree with the rest of the device.

FIG. 6 shows schematic representations of three different hand-held shock wave applicators:

(a) represents a linear hand-held shock wave applicator (17) according to the state of the art.

(b) represents an angular hand-held shock wave applicator (21) according to the invention, wherein the shock wave (13) emitting part (23) thereof forms an angle of 25 degree with the rest of the device;

(c) represents another angular hand-held shock wave applicator (22) according to the invention, wherein the shock wave (13) emitting part (23) thereof forms an angle of 90 degree with the rest of the device;

The invention is based on the principle that resorbable biomaterial pieces of small size in an area of active acute healing as generated by the application of shock waves leads to a resorption of such particles.

REFERENCES

1. Sanz M, Vignoletti F. Key aspects on the use of bone substitutes for bone regeneration of edentulous ridges. *Dent Mater.* 2015; 31:640-647.
2. Esposito M, Grusovin M G, Kwan S, Worthington H V, Coulthard P. Interventions for replacing missing teeth: bone augmentation techniques for dental implant treatment. *Cochrane database of systematic reviews.* 2008: CD003607.
3. Draenert F G, Huetzen D, Neff A, Mueller W E. Vertical bone augmentation procedures: basics and techniques in dental implantology. *Journal of biomedical materials research. Part A.* 2014; 102:1605-1613.
4. Fretwurst T, Spanou A, Nelson K, Wein M, Steinberg T, Stricker A. Comparison of four different allogeneic bone grafts for alveolar ridge reconstruction: a preliminary histologic and biochemical analysis. *Oral Surg Oral Med Oral Pathol Oral Radiol.* 2014; 118:424-431.
5. Zimmermann G, Moghaddam A. Allograft bone matrix versus synthetic bone graft substitutes. *Injury.* 2011; 42 Suppl 2:S16-21.
6. Draenert G F, Delius M. The mechanically stable steam sterilization of bone grafts. *Biomaterials.* 2007; 28:1531-1538.
7. Finkemeier C G. Bone-grafting and bone-graft substitutes. *Journal of Bone & Joint Surgery America.* 2002; 84-A:454-464.
8. Simion M, Nevins M, Rocchietta I, et al. Vertical ridge augmentation using an equine block infused with recombinant human platelet-derived growth factor-BB: a histologic study in a canine model. *Int J Periodontics Restorative Dent.* 2009; 29:245-255.
9. Muller W E, Wang X, Diehl-Seifert B, et al. Inorganic polymeric phosphate/polyphosphate as an inducer of alkaline phosphatase and a modulator of intracellular Ca2+ level in osteoblasts (SaOS-2 cells) in vitro. *Acta Biomaterialia.* 2011; 7:2661-2671.
10. Williams D. The continuing evolution of biomaterials. *Biomaterials.* 2011; 32:1-2.
11. Costello B J, Shah G, Kumta P, Sfeir C S. Regenerative medicine for craniomaxillofacial surgery. *Oral Maxillofac Surg Clin North Am.* 2010; 22:33-42.

12. Huebsch N, Mooney D J. Inspiration and application in the evolution of biomaterials. *Nature.* 2009; 462:426-432.
13. Luong-Van E, Grondahl L, Chua K N, Leong K W, Nurcombe V, Cool S M. Controlled release of heparin from poly(epsilon-caprolactone) electrospun fibers. *Biomaterials.* 2006; 27:2042-2050.
14. Delloye C, Cornu O, Druez V, Barbier O. Bone allografts: What they can offer and what they cannot. *J Bone Joint Surg Br.* 2007; 89:574-579.
15. Nissan J, Marilena V, Gross O, Mardinger O, Chaushu G. Histomorphometric analysis following augmentation of the posterior mandible using cancellous bone-block allograft. *J Biomed Mat Res A.* 2011e; 97 A:509-513.
16. Spin-Neto R, Landazuri Del Barrio R A, Pereira L A, Marcantonio R A, Marcantonio E, Marcantonio E, Jr. Clinical similarities and histological diversity comparing fresh frozen onlay bone blocks allografts and autografts in human maxillary reconstruction. *Clin Implant Dent Relat Res.* 2013; 15:490-497.
17. Khoury F, Hanser T. Mandibular bone block harvesting from the retromolar region: a 10-year prospective clinical study. *The International journal of oral & maxillofacial implants.* 2015; 30:688-397.
18. Gellrich N C, Held U, Schoen R, Pailing T, Schramm A, Bormann K H. Alveolar zygomatic buttress: A new donor site for limited preimplant augmentation procedures. *Journal of Oral & Maxillofacial Surgery.* 2007; 65:275-280.
19. Nissan J, Ghelfan O, Mardinger O, Calderon S, Chaushu G. Efficacy of cancellous block allograft augmentation prior to implant placement in the posterior atrophic mandible. *Clin Implant Dent Relat Res.* 2011a; 13:279-285.
20. Simion M, Jovanovic S A, Tinti C, Benfenati S P. Long-term evaluation of osseointegrated implants inserted at the time or after vertical ridge augmentation. A retrospective study on 123 implants with 1-5 year follow-up. *Clin Oral Implants Res.* 2001; 12:35-45.
21. Iglhaut G, Schwarz F, Grundel M, Mihatovic I, Becker J, Schliephake H. Shell technique using a rigid resorbable barrier system for localized alveolar ridge augmentation. *Clin Oral Implants Res.* 2014; 25:e149-154.
22. Schliephake H, Drewes M, Mihatovic I, Schwarz F, Becker J, Iglhaut G. Use of a self-curing resorbable polymer in vertical ridge augmentations—a pilot study in dogs. *Clin Oral Implants Res.* 2014; 25:435-440.
23. Urban I A, Jovanovic S A, Lozada J L. Vertical ridge augmentation using guided bone regeneration (GBR) in three clinical scenarios prior to implant placement: a retrospective study of 35 patients 12 to 72 months after loading. *Int J Oral Maxillofac Implants.* 2009; 24:502-510.
24. Delius M, Draenert K, Al Diek Y, Draenert Y. Biological effects of shock waves: in vivo effect of high energy pulses on rabbit bone. *Ultrasound Med Biol.* 1995; 21:1219-1225.

The invention claimed is:

1. A method for non-invasive fragmentation of residual biomaterial after bone augmentation, the method comprising:
generating shock waves;
applying the shock waves transdermally or intraorally; and
targeting the shock waves toward the residual biomaterial from the bone augmentation to fragment the residual biomaterial.
2. The method of claim 1, wherein the method is performed after an application in orthopedic surgery including bone augmentation with biomaterials.
3. The method of claim 1, wherein the method is performed after an application in dental implanatology including bone augmentation with biomaterials.
4. The method of claim 2, wherein the application in orthopedic surgery including bone augmentation with biomaterials is a surgery in a spine, a surgery to a tibia head, or a hip revision arthroplasty.
5. The method of claim 1, wherein generating the shock waves comprises generating the shock waves as pulsed shock waves.
6. The method of claim 1, further comprising focusing the shock waves toward the residual biomaterial.
7. The method of claim 3, further comprising applying the shock waves with an appropriately angulated device to target a desired area of an alveolar crest intraorally.
8. The method of claim 7, wherein an angle between a head of a shock wave generator generating the shock waves and a handle of the appropriately angulated device ranges between 25 and 90 degree.
9. The method of claim 1, wherein the residual biomaterial is osteoconductive with an interconnecting porous system.
10. The method of claim 1, wherein the residual biomaterial is resorbable.
11. The method of claim 5, further comprising focusing the pulsed shock waves toward the residual biomaterial.
12. The method of claim 5, further comprising applying the pulsed shock waves with the aid of an appropriately angulated device to target a desired area of the alveolar crest intraorally.
13. The method of claim 5, wherein an angle between a head of a shock wave generator generating the pulsed shock waves and a handle of the appropriately angulated device ranges between 25 and 90 degree.
14. The method of claim 5, wherein the residual biomaterial is osteoconductive with an interconnecting porous system.
15. The method of claim 5, wherein the residual biomaterial is resorbable.
16. The method of claim 5, wherein the pulsed shock waves are applied in fast repetition.
17. The method of claim 5, wherein the pulsed shock waves result in pressures between 30 and 150 MPa for 0.5-3 microseconds, after a rise time of around 10 ns.
18. The method of claim 5, wherein the pulsed shock waves result in pulse energies in a range of 10 to 100 mJ.
19. The method of claim 5, wherein the pulsed shock waves result in energy densities between about 0.2 and 2.0 $mJ/mm^2$, and wherein energy density is defined as an amount of acoustical energy transmitted through an area of 1 $mm^2$ per pulse.

* * * * *